US011986376B2

(12) United States Patent
Chen et al.

(10) Patent No.: US 11,986,376 B2
(45) Date of Patent: May 21, 2024

(54) DRESSING AND WOUND DETERMINATION SYSTEM

(71) Applicant: CYMMETRIK ENTERPRISE CO., LTD., Taipei (TW)

(72) Inventors: Sz-Hau Chen, Taipei (TW); Chun-Hsiang Yang, Taipei (TW)

(73) Assignee: CYMMETRIK ENTERPRISE CO., LTD., Taipei (TW)

(*) Notice: Subject to any disclaimer, the term of this patent is extended or adjusted under 35 U.S.C. 154(b) by 207 days.

(21) Appl. No.: 17/340,035

(22) Filed: Jun. 6, 2021

(65) Prior Publication Data

US 2022/0331165 A1 Oct. 20, 2022

(30) Foreign Application Priority Data

Apr. 14, 2021 (TW) .................. 110113438

(51) Int. Cl.
*A61F 13/00* (2024.01)
*A61L 15/24* (2006.01)
(52) U.S. Cl.
CPC ........ *A61F 13/00059* (2013.01); *A61L 15/24* (2013.01); *A61F 2013/00153* (2013.01)
(58) Field of Classification Search
CPC ................ A61F 13/00; A61F 13/00051; A61F 13/00059; A61F 13/00085;
(Continued)

(56) References Cited

U.S. PATENT DOCUMENTS

| 2008/0021423 A1* | 1/2008 | Klofta | A61F 13/42 600/300 |
| 2014/0121487 A1* | 5/2014 | Faybishenko | G16H 40/63 600/365 |

(Continued)

FOREIGN PATENT DOCUMENTS

| CN | 207306788 U | 5/2018 |
| CN | 210019931 U | 2/2020 |

OTHER PUBLICATIONS

Colour Spectrum, 2023, [online], [retrieved on Sep. 19, 2023]. Retrieved from the Internet <URL:https://byjus.com/chemistry/color-spectrum/#:~:text=The%20visible%20part%20of%20the,energy%20to%20lower%20energy%20values. (Year: 2023).*

(Continued)

*Primary Examiner* — Ophelia A Hawthorne
*Assistant Examiner* — Gina McCarthy
(74) *Attorney, Agent, or Firm* — Maschoff Brennan (57) ABSTRACT

The present disclosure provides a dressing configured to cover a wound. The dressing includes a substrate layer, a contact layer and a readable pattern layer. The substrate layer is light-permeable. The contact layer is located at a side of the substrate layer, and the contact layer is configured to contact the wound or skin around the wound. The readable pattern layer is disposed on the contact layer. The readable pattern layer includes a plurality of positioning marks and a plurality of colored cells. The positioning marks are configured to define an information area. The colored cells are located in the information areas, wherein at least part of the colored cells includes a biological indicator, and the positioning marks and the colored cells are visible through the substrate layer.

12 Claims, 7 Drawing Sheets

(58) Field of Classification Search
CPC .... A61F 13/00089; A61F 13/15; A61F 13/02; A61F 13/023; A61F 13/0243; A61F 13/0266; A61F 13/42; A61F 2013/00153; A61F 2013/15008; A61F 2013/421; A61F 2013/422; A61F 2013/423; A61F 2013/424; A61F 13/01034; A61F 13/01017; A61L 15/24; A61L 15/56; A61B 5/145; A61B 5/44; A61B 5/441; A61B 5/445; G16H 50/00; G16H 40/063; G06K 7/1473; G06K 19/06037
See application file for complete search history.

(56) References Cited

U.S. PATENT DOCUMENTS

| | | | | |
|---|---|---|---|---|
| 2016/0292486 | A1* | 10/2016 | Prusik | G06K 7/1473 |
| 2020/0188180 | A1* | 6/2020 | Akbari | A61F 13/01017 |
| 2020/0268559 | A1* | 8/2020 | Lafferty | A61F 13/01034 |
| 2020/0340802 | A1* | 10/2020 | Tyson, II | G06K 19/06037 |

OTHER PUBLICATIONS

Chinese Office Action dated Dec. 2, 2022 as received in application No. 202110446483.8.

* cited by examiner

DRESSING AND WOUND DETERMINATION SYSTEM

CROSS-REFERENCE TO RELATED APPLICATIONS

This non-provisional application claims priority under 35 U.S.C. § 119(a) on Patent Application No(s). 110113438 filed in Taiwan, R.O.C. on Apr. 14, 2021, the entire contents of which are hereby incorporated by reference.

TECHNICAL FIELD

The present disclosure relates to a dressing and a wound determination system, more particularly to a dressing having a readable pattern layer and a wound determination system for reading the readable pattern layer.

BACKGROUND

A dressing is a sterile pad or compress designed to be in direct contact with a wound to provide an environment for optimum wound healing and protect the wound from further harm. Generally, the use of a wound dressing can help to seal the wound, reduce the risk of infection, ease pain and ultimately help the wound heal more quickly and reduce scarring.

When the wound is covered, the patient cannot see the recovery of the wound until the next change of dressing, thus the patient is unable to know whether the wound is properly treated or getting worse. Without timely and appropriate reaction time and time again, it might impair wound healing, cause wound infection, and even lead to a failure over time.

SUMMARY

The present disclosure provides a dressing and a wound determination system that provide an approach for the user to know the current status of wound when the wound is covered.

According to one aspect of the present disclosure, a dressing is configured to cover a wound. The dressing includes a substrate layer, a contact layer, and a readable pattern layer. The substrate layer is light-permeable. The contact layer is located at a side of the substrate layer, and the contact layer is configured to contact the wound or skin around the wound. The readable pattern layer is disposed on the contact layer. The readable pattern layer includes a plurality of positioning marks and a plurality of colored cells. The positioning marks are configured to define an information area. The colored cells are located in the information area. At least part of the colored cells includes a biological indicator. The positioning marks and the colored cells are visible through the substrate layer.

According to another aspect of the present disclosure, a wound determination system includes a processing center, a reader, and the abovementioned dressing. The reader is in communication connection with the processing center. The readable pattern layer is readable by the reader, and the reader transmits an image of the readable pattern layer into the processing center for determination.

According to the dressing discussed above, the colored cells can reflect the current status of the wound through the color change, the user is allowed to observe the current status of the wound through the substrate layer with the naked eye. Accordingly, it is allowed to timely observe the actual status of the wound without removing the dressing.

According to the wound determination system discussed above, besides the colored cells can be observed with the naked eye, the readable pattern layer can also be read by the reader. The processing center can determine the wound according to the indication status of the biological indicator of the colored cells and then can provide helpful suggestion about wound care.

BRIEF DESCRIPTION OF THE DRAWINGS

The present disclosure will become more fully understood from the detailed description given hereinbelow and the accompanying drawings which are given by way of illustration only and thus are not intending to limit the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
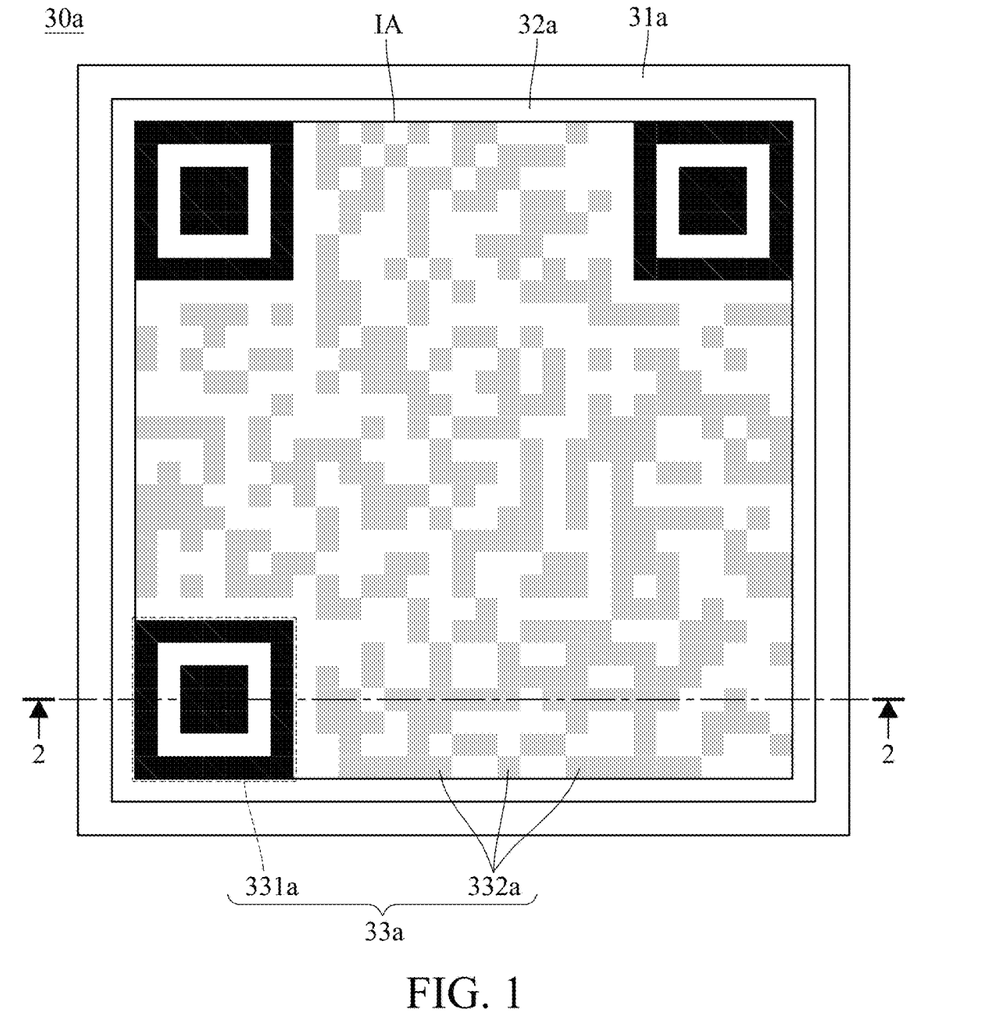
FIG. 1 is a top view of a dressing according to an embodiment of the present disclosure.
Figure 2:
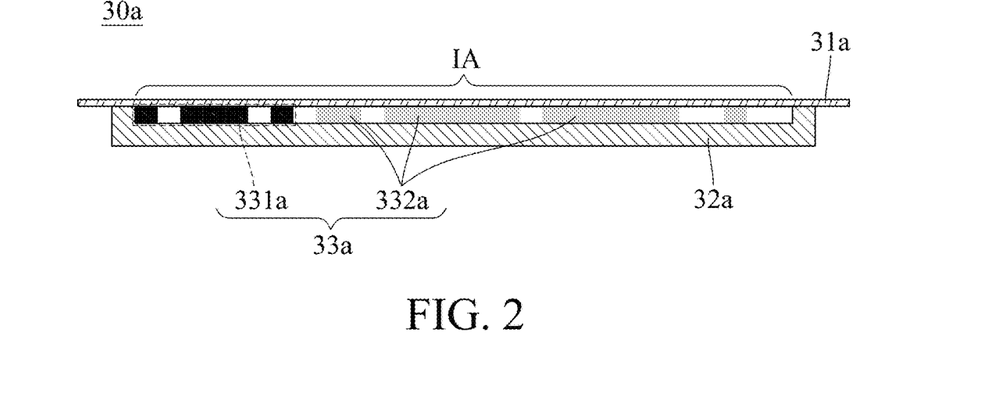
FIG. 2 is a cross-sectional view of the dressing along line 2-2 in FIG. 1.

Please refer to FIG. 1 and FIG. 2, where FIG. 1 is a top view of a dressing according to an embodiment of the present disclosure, and FIG. 2 is a cross-sectional view of the dressing along line 2-2 in FIG. 1.

One embodiment of the present disclosure provides a dressing 30a configured to cover a wound (not shown). The dressing 30a includes a substrate layer 31a, a contact layer 32a, and a readable pattern layer 33a. The substrate layer 31a is made of light-permeable material, thus it allows light to pass through. The material of the substrate layer 31a is, but not limited to be polyurethane (PU), thermoplastic polyurethanes (TPU), biocellulose, lignocellulose, phenol formaldehyde resin (PF), derivative of polyurethanes (e.g., polyester urethane (AU), polyether urethane (EU), and polyurethane (PU)), or polyvinyl alcohol fiber (PVA fiber).

The contact layer 32a is located at one side of the substrate layer 31a. The contact layer 32a may be made of woven or non-woven fibers of cotton, rayon, polyester, or any suitable material typically used in sterile gauze. The contact layer 32a is configured to directly contact the wound or the skin around the wound to promote healing and protect the wound from further harm. In this and some embodiments, the contact layer 32a may further contain or may be used with a topical medication or a wound membrane to cover the wound. Optionally, there may be an adhesive layer (not shown) arranged on the outer surface of the substrate layer 31a or the contact layer 32a, allowing the dressing 30a to be attached to the wound or the skin around the wound. Alternatively, at least one of the substrate layer 31a and the contact layer 32a may contain an adhesive material therein, such as acrylate or acrylic acid copolymer, allowing the dressing 30a to be self-attached to the wound or the skin around the wound. Note that the dressing 30a of the present disclosure may be non-adhesive; in such a case, the dressing 30a may be firmly attached to the skin by using any suitable medical paper tape.

In this embodiment, the readable pattern layer 33a is disposed on the contact layer 32a. In specific, in this and some embodiments of the present disclosure, the readable pattern layer 33a is disposed at the side of the contact layer 32a facing the substrate layer 31a; as shown, the readable pattern layer 33a is located between the contact layer 32a and the substrate layer 31a. Since the substrate layer 31a is light-permeable, the readable pattern layer 33a is visible through the substrate layer 31a. Note that the location of the readable pattern layer 33a may be modified as required; in some other embodiments, the readable pattern layer may be disposed within the contact layer if the contact layer is light-permeable; in still some other embodiment, the readable pattern layer may be arranged at the side of the contact layer facing away from the substrate layer if the contact layer is light-permeable, and the readable pattern layer is still visible through the substrate layer and contact layer.

The readable pattern layer 33a may be employed as a data carrier. In this embodiment, the readable pattern layer 33a has, for example, one or more two-dimensional machine-readable label, such as a quick response code (QR code) that contains information to provide easy access through a suitable reader tool. As shown, the readable pattern layer 33a includes a plurality of positioning marks 331a and a plurality of colored cells 332a that are encoded into the binary numbers based on the encoding rule. The positioning marks 331a are provided for position and orientation detection, thus the positioning marks 331a are able to define an information area IA. The positioning marks 331a may be three colored squares respectively located at three corners of the information area IA, as shown, the arrangement of the positioning marks 331a define the lengths and the diagonal distance of the contour of the information area IA. The colored cells 332a are located within the information area IA. In this and some embodiments of the present disclosure, the positioning marks 331a and all of the colored cells 332a form a machine readable pattern. It can also be considered that the positioning marks 331a, all of the colored cells 332a and the blank part within the information area IA form a matrix (i.e., a standard QR code structure) that contains information about the current status of the wound which it is attached. For example, the information contained in the QR code structure may contain the brand name, facts about the product features, the manufacturer, the date of product manufacture, the ingredients of the topical medication, and/or the instruction for use; alternatively, the information may only contain data for a suitable reader tool that points to a related website or application. Note that the data contained in the information may be changed, added, or reduced as required.

In this embodiment, at least part of the colored cells 332a includes a biological indicator. In this and some embodiments of the present disclosure, all of the colored cells 332a include the biological indicator. The biological indicator can visually respond to the change of the wound recovery. In specific, the examples of the biological indicator may be made of the material typically used in an acid-base indicator, a chemical indicator, a bacterial indicator, an endospore indicator, a protein indicator, a peptide indicator, a DNA indicator, or an enzyme indicator. In this and some embodiments of the present disclosure, the biological indicator is exemplarily made of the material typically used in the acid-base indicator; in this case, when the wound is infected, the pH value of the tissue fluid from the wound may change, the tissue fluid will be absorbed into the readable pattern layer 33a through the contact layer 32a, and then the colored cells 332a of the readable pattern layer 33a will change their color while interacting with the tissue fluid.

Figure 3:
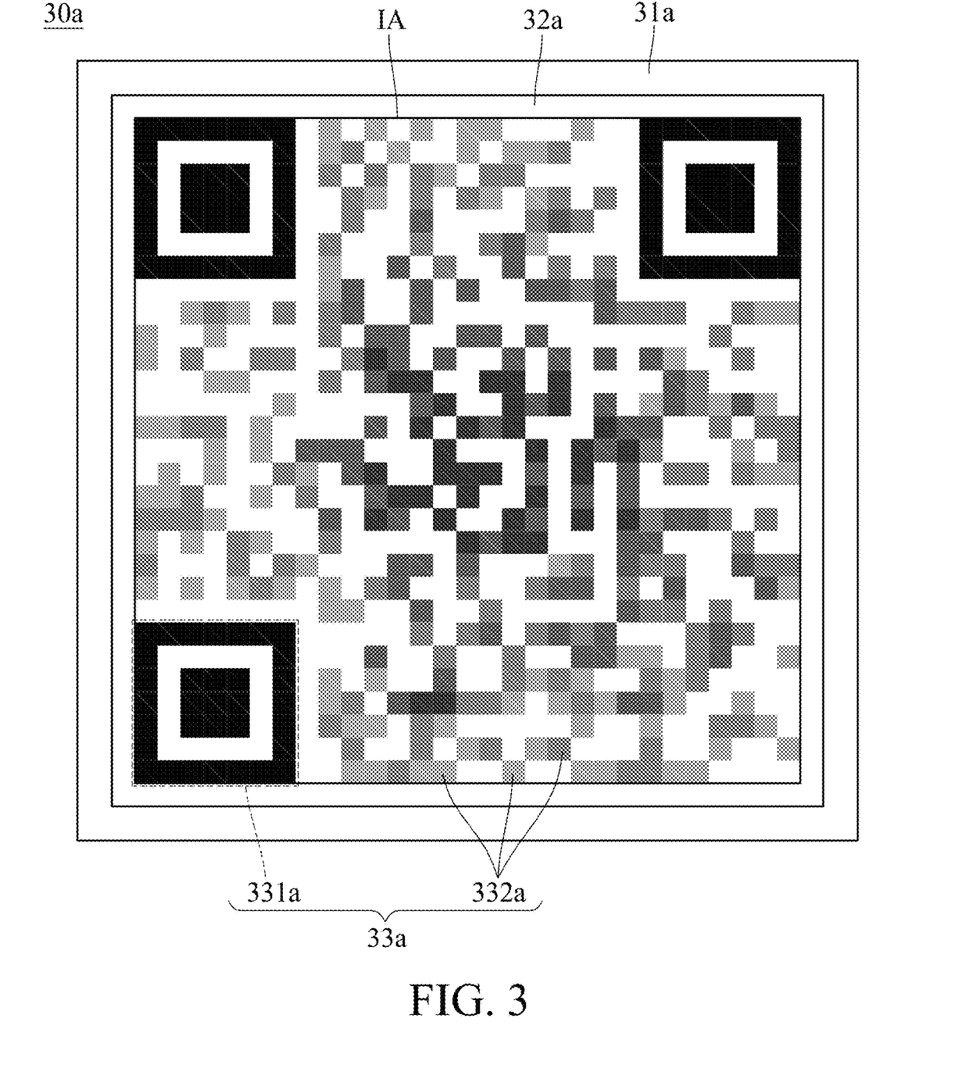
FIG. 3 is a top view of the dressing in FIG. 1 showing that a biological indicator of the dressing has changed its color.
Figure 4:
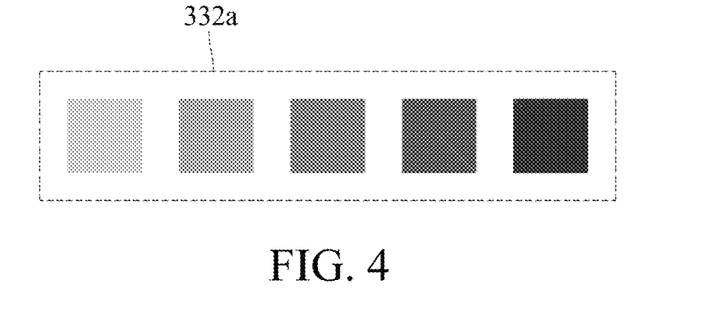
FIG. 4 is a color chart showing the color shade of the biological indicator of the dressing in FIG. 1.

Please further refer to FIG. 3 to FIG. 4, where FIG. 3 is a top view of the dressing in FIG. 1 showing that a biological indicator of the dressing has changed its color, and FIG. 4 is a color chart showing the color shade of the biological indicator of the dressing in FIG. 1. Regarding FIG. 1 and FIG. 3, FIG. 1 depicts a dressing 30a not yet used on a wound, and FIG. 3 depicts the dressing 30a that absorbs tissue fluid from a wound. In detail, in FIG. 3, the tissue fluid from the wound can be absorbed to the readable pattern layer 33a through the contact layer 32a, the color of some of the colored cells 332a within the information area IA may change when interacting with the tissue fluid, while the positioning marks 331a remain their original color. With further reference to FIG. 4, the more acidity/basicity in the tissue fluid interacting with the colored cells 332a, the darker color the colored cells 332a become. As such, the colored cells 332a can reflect the current status of the wound through the color change. For example, in FIG. 4, the leftmost block may represent the color shade of the biological indicator that is not yet used on a wound, the second block from the left side may represent the color shade of the biological indicator that is attached to an uninfected wound, and the three remaining blocks may represent, from the left to the right, the color shades of the biological indicators that are attached to wounds of mild infection, moderate infection, and severe infection, respectively.

According to the dressing 30a discussed above, the user is allowed to observe the current status of the wound through the light-permeable substrate layer 31a with the naked eye. Also, the color gradient of the colored cells 332a somehow reveals the infected area in the wound. Accordingly, it is allowed to timely observe the actual status of the wound without removing the dressing 30a.

For example, the infection degree of the wound can be presumed according to the color shades of the colored cells 332a, or the infection area of the wound can be presumed according to the color change area of the colored cells 332a. The user can preliminarily determine whether it is necessary to change the dressing 30a or make a return visit.

Note that there are other suitable options for the material for the biological indicator to respond to the status change of the tissue fluid from the wound. For example, in some other embodiments, the material of the biological indicator may be one typically used in a bacterial indicator that changes its color in response to the amount of a specific bacterial species; in such a case, the colored cells are able to reflect the severity and area of the infection in the wound according to the amount of a specific bacterial species. In still some other embodiments, the material of the biological indicator may be one typically used in an endospore indicator that changes its color in response to the amount of the special dormant and non-reproductive structures generated by a specific bacterial species; in such a case, the colored cells are able to reflect the severity and area of the infection in the wound according to the amount of the special dormant and non-reproductive structures. However, the present disclosure is not limited thereto. In still further some other embodiments, the material of the biological indicator may be one typically used in a microbial indicator that changes color in response to the amount of microbe such as fungus, virus, pathogenic protein particles, etc.

Figure 5:
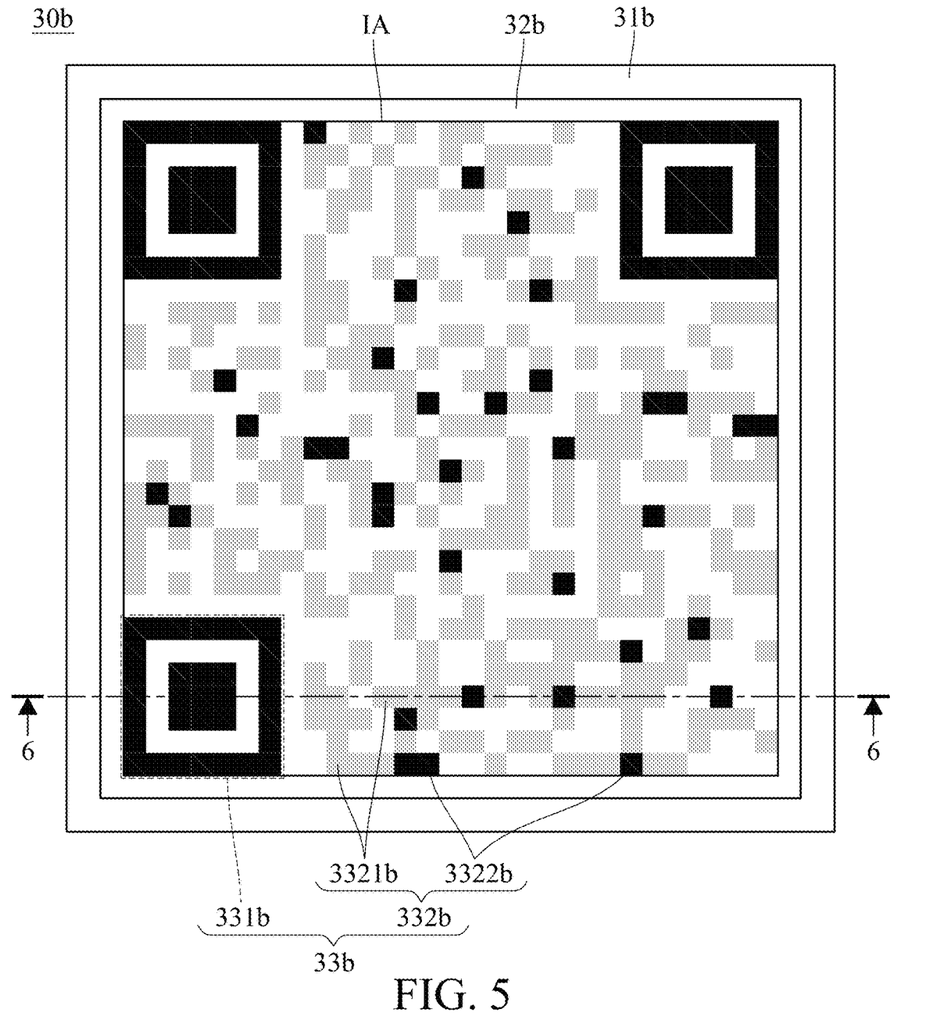
FIG. 5 is a top view of a dressing according to another embodiment of the present disclosure.
Figure 6:
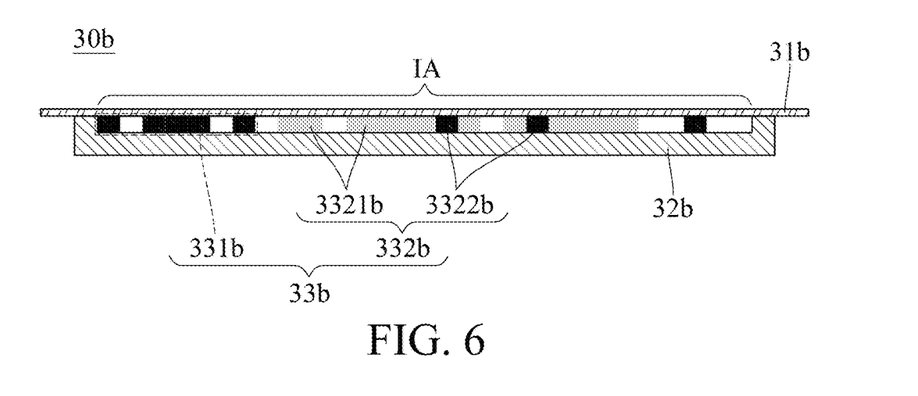
FIG. 6 is a cross-sectional view of the dressing along line 6-6 in FIG. 5.

Please refer to FIG. 5 to FIG. 6, where FIG. 5 is a top view of a dressing according to another embodiment of the present disclosure, and FIG. 6 is a cross-sectional view of the dressing along line 6-6 in FIG. 5. One embodiment of the present disclosure provides a dressing 30b configured to cover a wound (not shown). The dressing 30b includes a substrate layer 31b, a contact layer 32b, and a readable pattern layer 33b. The features such as the structure and the relative position of the substrate layer 31b are similar to that of the substrate layer 31a in the embodiment of FIG. 1. The features such as the structure and the relative position of the contact layer 32b are similar to that of the contact layer 32a in the embodiment of FIG. 1. The features such as the structure and the relative position of the readable pattern layer 33b are similar to that of the readable pattern layer 33a in the embodiment of FIG. 1. Note that only differences between this embodiment and the embodiment of FIG. 1 will be described hereinafter.

In this and some embodiments of the present disclosure, the colored cells 332b of the readable pattern layer 33b are divided into a first group 3321b and a second group 3322b that are randomly distributed within the information area IA. The first group 3321b of the colored cells 332b includes a biological indicator that can visually respond to the change of the wound recovery, while the second group 3322b of the colored cells 332b includes the same material as the normal black paint of the positioning marks 331b. The positioning marks 331b, the first group 3321b of the colored cells 332b, and the second group 3322b of the colored cells 332b form a machine readable pattern that contains information.

The paint of the second group 3322b of the colored cells 332b does not interact with the tissue fluid from the wound, therefore the second group 3322b of the colored cells 332b can maintain its original color and thus retain a certain degree of machine readability of the readable pattern layer 33b.

Note that FIG. 5 and FIG. 6 show the unused dressing 30b with no color change. For the color change condition of the biological indicator of the first group 3321b of the colored cells 332b caused by interaction with the tissue fluid from the wound, please refer to the above description of FIG. 4.

Figure 7:
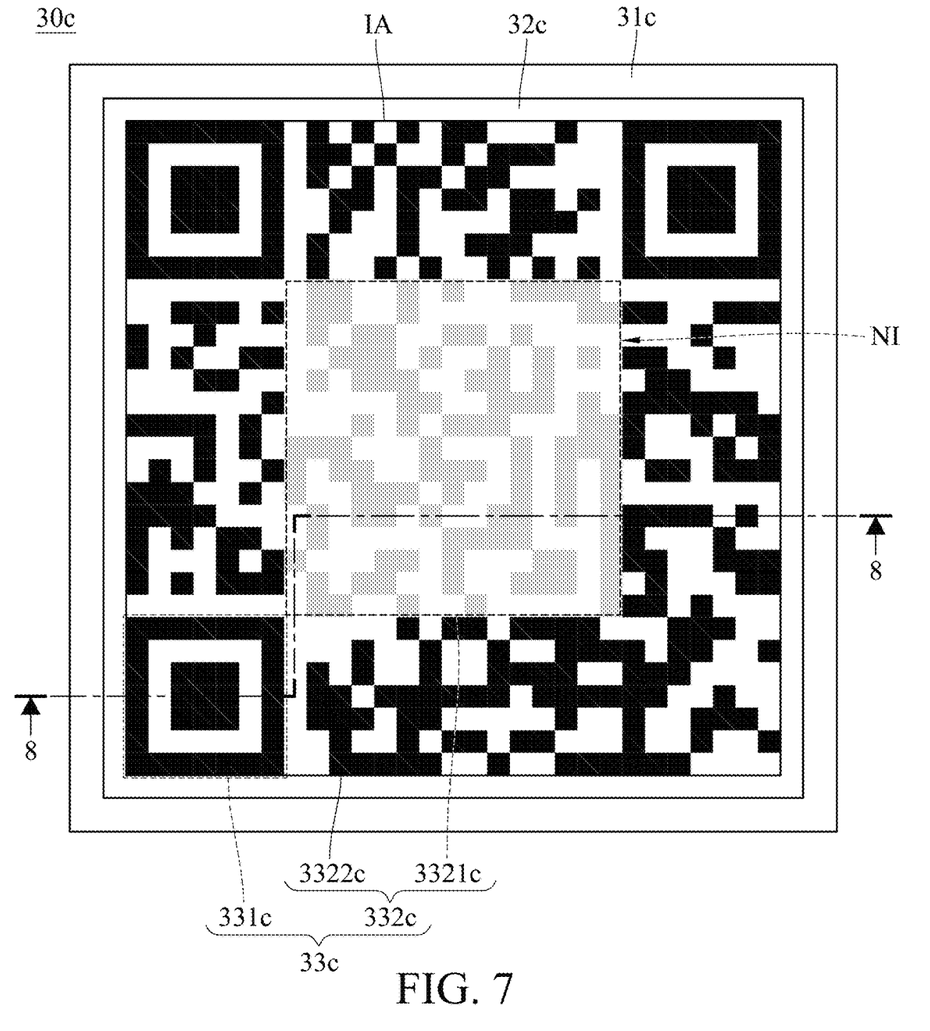
FIG. 7 is a top view of a dressing according to further another embodiment of the present disclosure.
Figure 8:
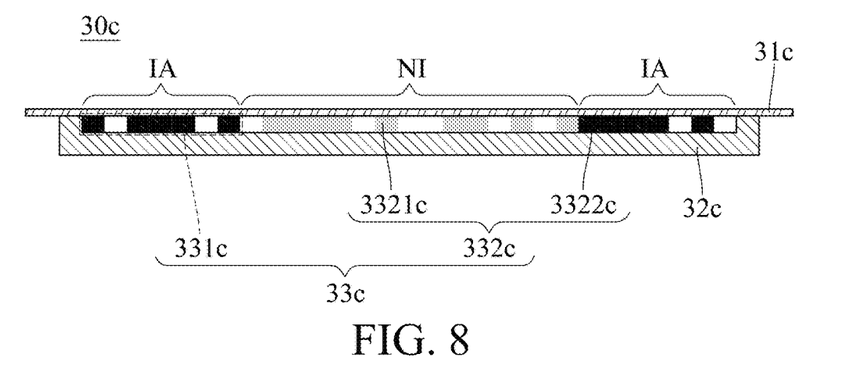
FIG. 8 is a cross-sectional view of the dressing along line 8-8 in FIG. 7.

Please refer to FIG. 7 to FIG. 8, where FIG. 7 is a top view of a dressing according to further another embodiment of the present disclosure, and FIG. 8 is a cross-sectional view of the dressing along line 8-8 in FIG. 7. One embodiment of the present disclosure provides a dressing 30c configured to cover a wound (not shown). The dressing 30c includes a substrate layer 31c, a contact layer 32c, and a readable pattern layer 33c. The features such as the structure and the relative position of the substrate layer 31c are similar to that of the substrate layer 31a in the embodiment of FIG. 1. The features such as the structure and the relative position of the contact layer 32c are similar to that of the contact layer 32a in the embodiment of FIG. 1. The features such as the structure and the relative position of the readable pattern layer 33c are similar to that of the readable pattern layer 33a in the embodiment of FIG. 1. Note that only differences between this embodiment and the embodiment of FIG. 1 will be described hereinafter.

In this and some embodiments of the present disclosure, the colored cells 332c of the readable pattern layer 33c are divided into a first group 3321c and a second group 3322c. The first group 3321c of the colored cells 332c may be located in the central portion of the readable pattern layer 33c, while the second group 3322c of the colored cells 332c may be located in the peripheral portion of the readable pattern layer 33c. Since the QR code is designed to have error correction capacity, some portions in the matrix of the QR code may not need to store effective data information. Referring to the matrix of the QR code in FIG. 7, the central portion of the matrix is a non-information area NI where no effective data information is stored, while the remaining peripheral portion of the matrix is an information area IA where effective data information is stored. Therefore, the central portion (non-information area NI) of the QR code can be used for containing a biological indicator, and the peripheral portion (information area IA) of the QR code can be used for containing effective data information. In specific, the first group 3321c of the colored cells 332c include the biological indicator, the second group 3322c of the colored cells 332c and the positioning marks 331c include normal paint, and the second group 3322c of the colored cells 332c and the positioning marks 331c form a machine readable pattern that contains effective data information. As discussed above, the biological indicator of the first group 3321c of the colored cells 332c can reflect the current status of the wound through the color change, and the user is allowed to observe that through the light-permeable substrate layer 31c with the naked eye. Accordingly, it is allowed to timely observe the actual status of the wound without removing the dressing 30c. Also, the machine readability of the readable pattern layer 33c may not be affected.

Note that FIG. 7 and FIG. 8 show the unused dressing 30c with no color change. For the color change condition of the biological indicator of the first group 3321c of the colored cells 332c caused by interaction with the tissue fluid from the wound, please refer to the above description of FIG. 4.

Figure 9:
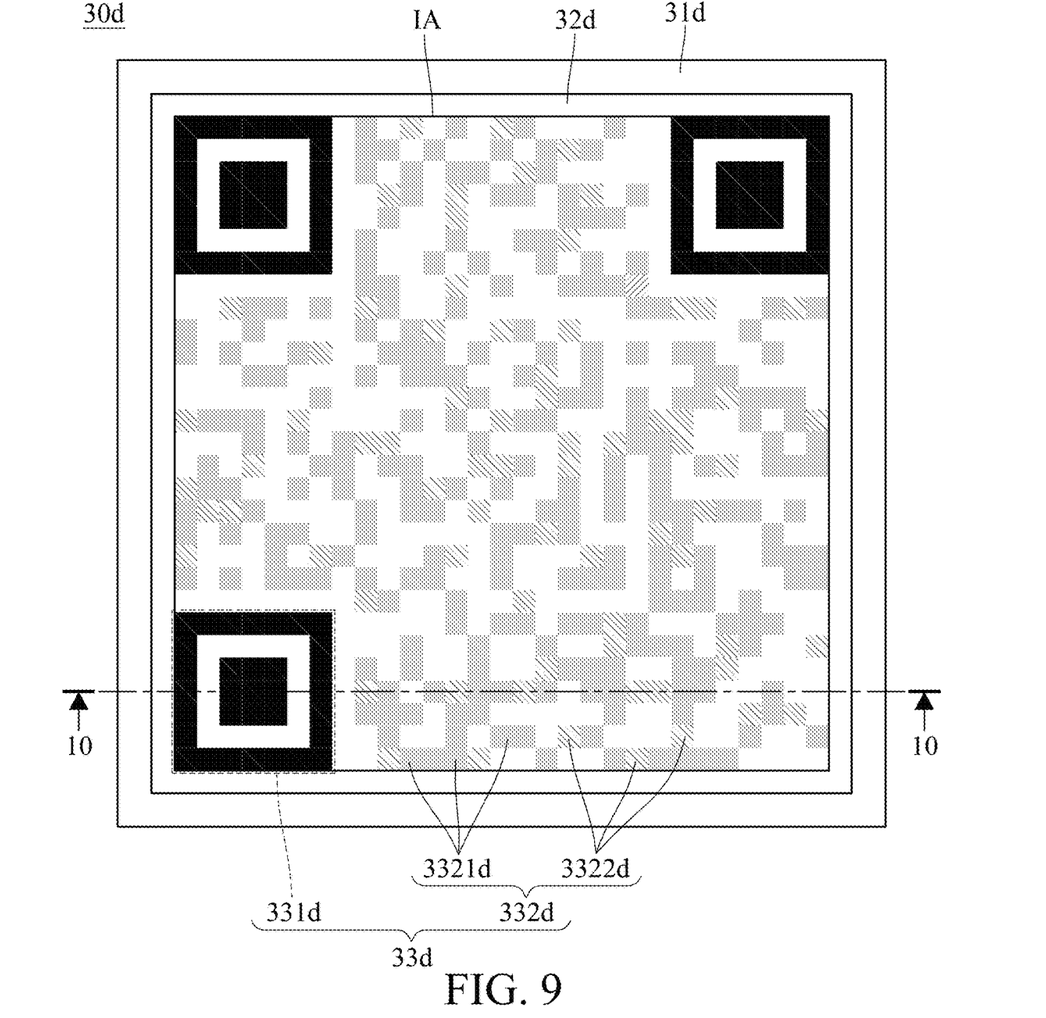
FIG. 9 is a top view of a dressing according to still another embodiment of the present disclosure.
Figure 10:
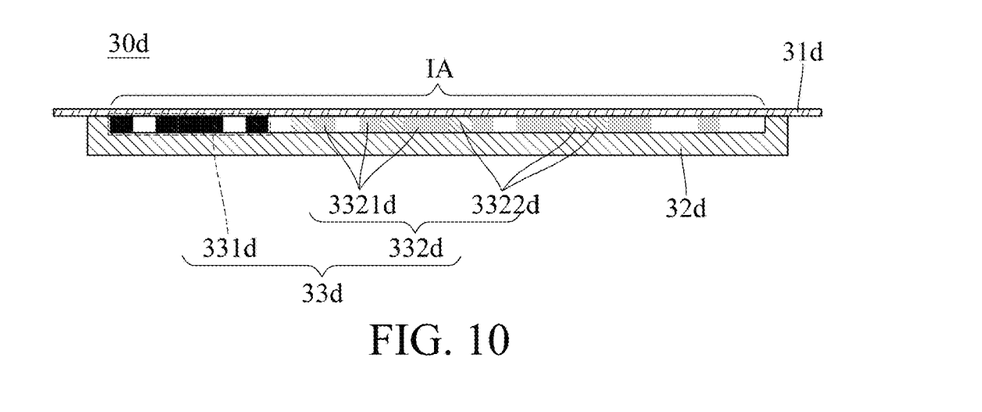
FIG. 10 is a cross-sectional view of the dressing along line 10-10 in FIG. 9.

Please refer to FIG. 9 to FIG. 10, where FIG. 9 is a top view of a dressing according to still another embodiment of the present disclosure, and FIG. 10 is a cross-sectional view of the dressing along line 10-10 in FIG. 9. One embodiment of the present disclosure provides a dressing 30d configured to cover a wound (not shown). The dressing 30d includes a substrate layer 31d, a contact layer 32d, and a readable pattern layer 33d. The features such as the structure and the relative position of the substrate layer 31d are similar to that of the substrate layer 31a in the embodiment of FIG. 1. The features such as the structure and the relative position of the contact layer 32d are similar to that of the contact layer 32a in the embodiment of FIG. 1. The features such as the structure and the relative position of the readable pattern layer 33d are similar to that of the readable pattern layer 33a in the embodiment of FIG. 1. Note that only differences between this embodiment and the embodiment of FIG. 1 will be described hereinafter.

In this and some embodiments of the present disclosure, the colored cells 332d of the readable pattern layer 33d are divided into a first group 3321d and a second group 3322d that are randomly distributed within the information area IA. The first group 3321d of the colored cells 332d includes a first biological indicator, and the second group 3322d of the colored cells 332d include a second biological indicator. The positioning marks 331d, the first group 3321d of the colored cells 332d, and the second group 3322d of the colored cells 332d form a machine readable pattern that contains information.

The first biological indicator and the second biological indicator will react according to different conditions. In detail, the first biological indicator may be made of the material typically used in an acid-base indicator, and the second biological indicator may be made of the material typically used in a bacterial indicator. The first group 3321d and the second group 3322d of the colored cells 332d will generate two types of color change reactions according to the pH value of and the amount of a specific bacterial species in the tissue fluid from the infected wound, as discussed above.

Figure 11:
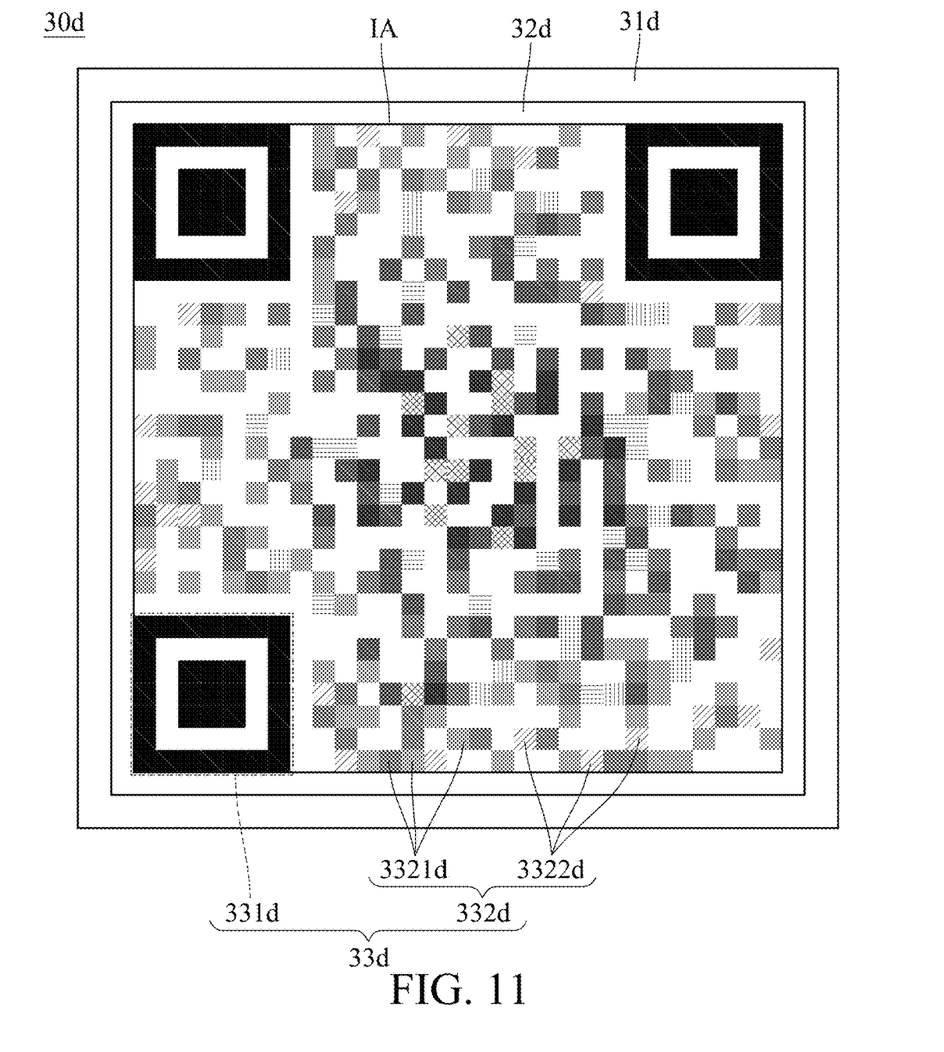
FIG. 11 is a top view of the dressing in FIG. 9 showing that biological indicators of the dressing have changed their color.
Figure 12:
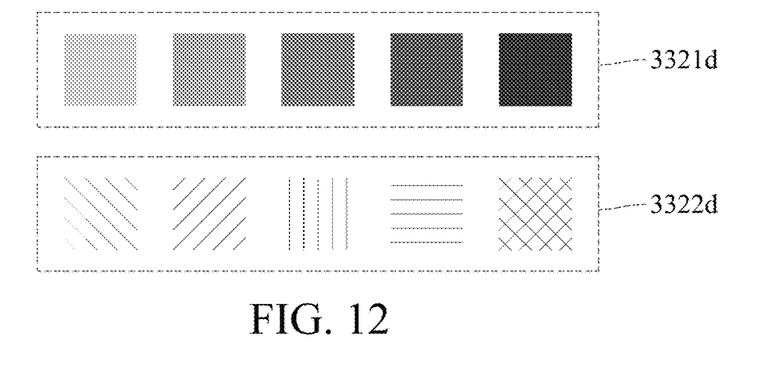
FIG. 12 is a color chart showing the color shade of each of the biological indicators of the dressing in FIG. 9.

Please further refer to FIG. 11 to FIG. 12, where FIG. 11 is a top view of the dressing in FIG. 9 showing that biological indicators of the dressing have changed their color, and FIG. 12 is a color chart showing the color shade of each of the biological indicators of the dressing in FIG. 9. Regarding FIG. 9 and FIG. 11, FIG. 9 depicts a dressing 30d not yet used on a wound, and FIG. 11 depicts the dressing 30d that absorbs tissue fluid from a wound. In detail, in FIG. 11, the tissue fluid from the wound can be absorbed to the readable pattern layer 33d through the contact layer 32d to generate two types of color change reactions between the tissue fluid and the first biological indicator and between the tissue fluid and the second biological indicator. Specifically, the pH value of the tissue fluid causes some of the first group 3321d of the colored cells 332d within the information area IA to change its color, the amount of a specific bacterial species in the tissue fluid causes some of the second group 3322d of the colored cells 332d within the information area IA to change its color. With further reference to FIG. 12, the five blocks in the upper row denote color shades of the first group 3321d, and they may be the same as the five blocks in FIG. 4, which represent, from the left to the right, the colors of the first group 3321d that is not yet used on a wound, attached to wounds with no infection, mild infection, moderate infection, and severe infection, respectively. In FIG. 12, the five blocks in the lower row use different types of hatching lines to denote color shades of the second group 3322d, where the leftmost block may represent the color of the second group 3322d that is not yet used on a wound, the second block from the left side may represent the color of the second group 3322d attached to a wound where a specific bacterial species is not reproduced, and the three remaining blocks may represent, from the left to the right, the color of the second group 3322d attached to a wound where a small amount of specific bacterial species is reproduced, the color of the second group 3322d attached to a wound where a medium amount of specific bacterial species is reproduced, and the color of the second group 3322d attached to a wound where a large amount of specific bacterial species is reproduced, respectively. Note that every color of the first group 3321d and every color of the second group 3322d are different. And, for simplicity, different types of hatching lines are used in FIG. 12 for denoting different color shades of the second group 3322d. However, in practical applications, the color change reaction of the second group 3322d can still be represented in different colors. For example, the types of hatching lines in the blocks of the lower row of FIG. 12, from the left to the right, may correspond to green, brown, red, blue, and orange colors. In FIG. 12, the closer to the right side the block of the lower row is, the larger amount of specific bacterial species the block represents.

According to the dressing 30d discussed above, the first group 3321d and the second group 3322d will generate color change reactions according to two different conditions, and colors of the first group 3321d and the second group 3322d are different from one another. As such, the first group 3321d and the second group 3322d can reflect different status of the wound through the color change, and the user is allowed to observe that through the light-permeable substrate layer 31d. Also, the color gradient of the first group 3321d and the second group 3322d somehow reveal the infected area in the wound. Accordingly, it is allowed to timely observe the actual status of the wound without removing the dressing 30d.

For example, the infection degree of the wound can be presumed according to the color shades of the first group 3321d of the colored cells 332d, the infection area of the wound can be presumed according to the color change area of the first group 3321d of the colored cells 332d, the reproduction amount of a specific bacterial species on the wound can be roughly estimated according to the type of hatching lines (or the color shades different from all color shades of the first biological indicator) of the second group 3322d of the colored cells 332d, or the reproduction area of a specific bacterial species on the wound can be roughly estimated according to the distribution area of hatching lines (or the distribution area of all colors of the second biological indicator different from all colors of the first biological indicator) of the second group 3322d of the colored cells 332d. Accordingly, the user can preliminarily determine whether it is necessary to change the dressing 30d or make a return visit.

Figure 13:
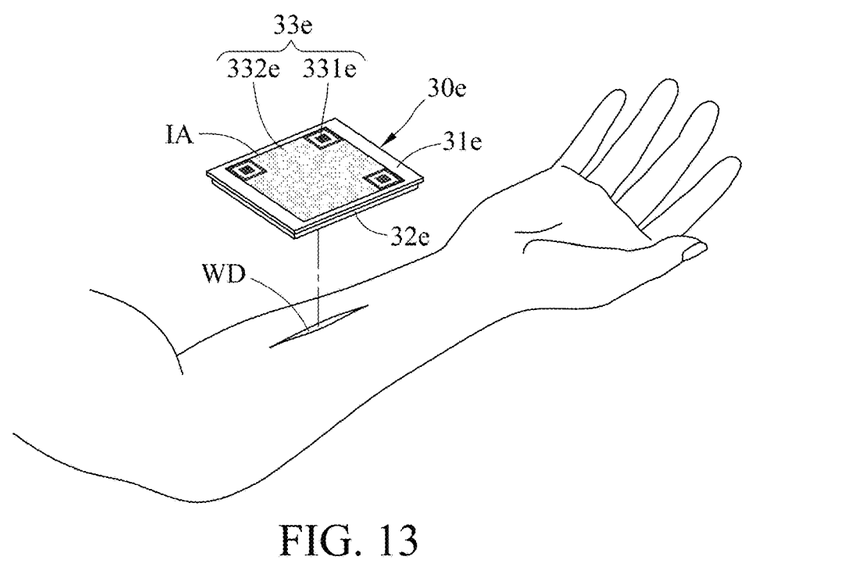
FIG. 13 is a schematic view showing a use scenario of a dressing of a wound determination system according to still further another embodiment of the present disclosure.
Figure 14:
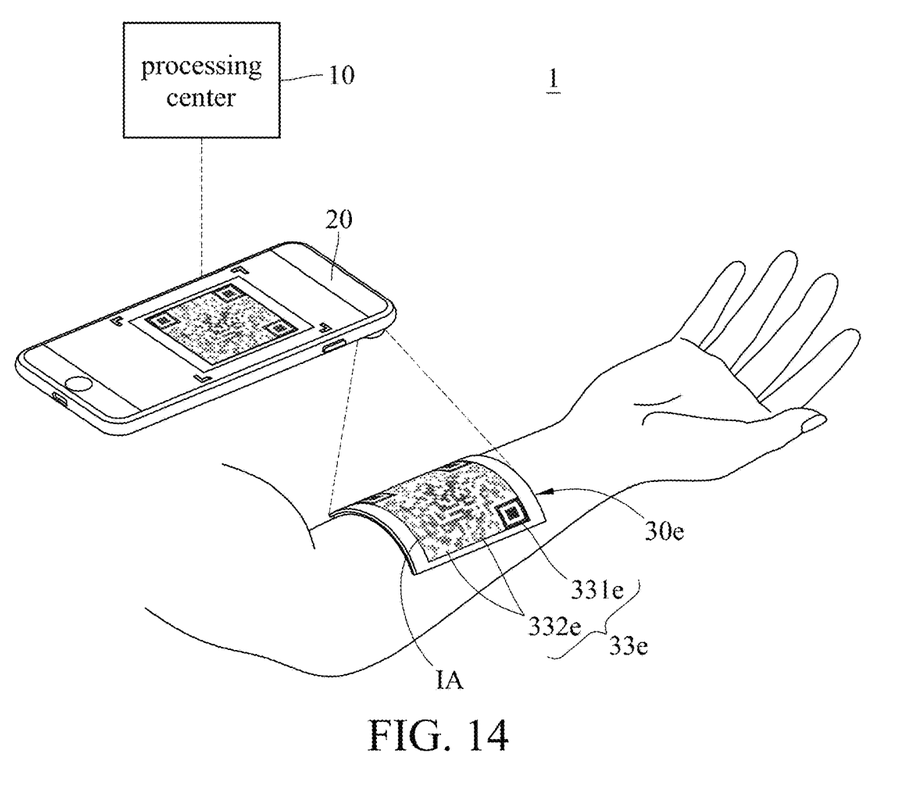
FIG. 14 is a schematic view showing the use of the dressing of the wound determination system of FIG. 13.

Please refer to FIG. 13 to FIG. 14, where FIG. 13 is a schematic view showing a use scenario of a dressing of a wound determination system according to still further another embodiment of the present disclosure, and FIG. 14 is a schematic view showing the use of the dressing of the wound determination system of FIG. 13.

As shown in FIG. 13, a dressing 30e configured to cover a wound WD is provided. The dressing 30e includes a substrate layer 31e, a contact layer 32e, and a readable pattern layer 33e. The dressing 30e may be the same as one of the dressings 30a to 30d in the embodiments of FIGS. 1 to 12. That is, the substrate layer 31e, the contact layer 32e, and the readable pattern layer 33e can respectively correspond to one of the substrate layer s 31a to 31d, one of the contact layers 32a to 32d, and one of the readable pattern layers 33a to 33d in the embodiments of FIGS. 1 to 12. Hereinafter, the dressing 30e corresponding to the dressing 30a of the embodiment of FIG. 1 is an example for the description of this embodiment, and the features such as the structure and the relative position of the substrate layer 31e, the contact layer 32e, and the readable pattern layer 33e of the dressing 30e will not be provided again.

As shown in FIG. 14, a wound determination system 1 is provided. The wound determination system 1 includes a processing center 10, a reader 20, and the abovementioned dressing 30e. The processing center 10 may be a cloud medical care center. The reader 20 may be a smartphone or any suitable smart device with camera. The reader 20 is in communication connection with the processing center 10 via wireless or wired manner. The dressing 30e covers the wound WD. The reader 20 is able to capture the image of the readable pattern layer 33e and send it to the processing center 10 so that the reader 20 or the processing center 10 can obtain the information contained in the readable pattern layer 33e; as discussed, the information may contain the brand name, facts about the product features, the manufacturer, the date of product manufacture, the ingredients of the topical medication, and/or the instruction for use.

In FIG. 14, while the contact layer 32e contacts the wound WD or the skin around the wound WD, as discussed above, the biological indicator can change its color to be a different shade according to the status of the wound WD such as the pH value of the tissue fluid from the wound WD or the reproduction amount of a specific bacterial species on the wound WD. Besides the color change degree of the colored cells 332e can be seen with the naked eye, the readable pattern layer 33e can also be scanned and read by the reader 20. The processing center 10 can determine the infection degree of the wound WD through the reader 20 according to the color shades of the colored cells 332e of the readable pattern layer 33e and then can determine a result of infection degree of the wound WD. If the result of the infection degree exceeds a threshold pre-stored in the processing center 10, the processing center 10 generates a reminder signal. The reminder signal may be a text message sent to the reader 20, and the user can make a proper decision such as changing the dressing 30e or making a return visit when reading the reminder signal.

Also, the processing center 10 can further calculate the infection area of the wound WD. In detail, the area information of each positioning mark 331e of the dressing 30e is pre-stored in the processing center 10 when the dressing 30e is manufactured. When the processing center 10 receives the image of the color-changed readable pattern layer 33e transmitted from the reader 20, the processing center 10 can calculate a color change area information of the color-changed colored cells 332e with different shades based on the area information of the positioning marks 331e and then can determine a result of infection area of the wound WD. If the result of the infection area exceeds a threshold pre-stored in the processing center 10, the processing center 10 generates another reminder signal. The another reminder signal, similar to the abovementioned reminder signal, may be a text message sent to the reader 20, and the user can make a proper decision such as changing the dressing 30e or making a return visit after reading the another reminder signal. The description of the determination of the processing center 10 in generating the reminder signal based on the infection degree or the infection area of the wound WD is only exemplary. However, the present disclosure is not limited thereto. In some other embodiments, the processing center may generate a reminder signal after comprehensively analyzing the infection degree and the infection area.

In this and some embodiments of the present disclosure, besides the processing center 10 can determine the infection degree and the infection area according to the color change degree of the colored cells 332e, the processing center 10 can also determine the remaining effective time of the dressing 30e based on the color change degree and the expiration date so as to remind the user to change the dressing 30e in the remaining effective time. If the wound WD is in a good recovery status, the processing center 10 can also determine the healing degree and the remaining recovery time of the wound WD according to the current status of the wound WD. As the reader 20 continuously transmitting the image of the readable pattern layer 33e of the dressing 30e into the processing center 10, the processing center 10 can track the recovery condition of the wound WD and then can timely provide helpful suggestion about wound care.

According to the dressing discussed above, the colored cells can reflect the current status of the wound through the color change, the user is allowed to observe the current status of the wound through the substrate layer with the naked eye. Accordingly, it is allowed to timely observe the actual status of the wound without removing the dressing.

According to the wound determination system discussed above, besides the colored cells can be observed with the naked eye, the readable pattern layer can also be read by the reader. The processing center can determine the wound according to the indication status of the biological indicator of the colored cells and then can provide helpful suggestion about wound care.

The communication connection mentioned in the present disclosure refers to a connection manner that two components are able to exchange data with each other by, for example, wireless transmission.

The embodiments are chosen and described in order to best explain the principles of the present disclosure and its practical applications, to thereby enable others skilled in the art best utilize the present disclosure and various embodiments with various modifications as are suited to the particular use being contemplated. It is intended that the scope of the present disclosure is defined by the following claims and their equivalents.

What is claimed is:

1. A dressing, configured to cover a wound, comprising: a substrate layer, being light-permeable; a contact layer, located at a side of the substrate layer, wherein the contact layer is configured to contact the wound or skin around the wound; and a readable pattern layer, disposed on the contact layer, comprising: a plurality of positioning marks, configured to define an information area, wherein the plurality of positioning marks comprises three colored squares respectively located at three corners of the information area, two of the three colored squares define an edge of a contour of the information area, most distant two of the three colored squares define a diagonal distance of the contour of the information area; and a plurality of colored cells, located within the information area, wherein at least part of the plurality of colored cells comprises a biological indicator, and the plurality of positioning marks and the plurality of colored cells are visible through the substrate layer; wherein the plurality of colored cells having at least part comprising the biological indicator are partially located between a space between the two of the three colored squares located at corners of the information area and defining the edge of the contour of the information area; wherein machine readable information stored within the edge of the contour of the information area defined by the two of the three colored squares remains a same during reaction of the biological indicator where the biological indicator changes color thereof to represent at least five different color shades; wherein a first part of a plurality of blank non-colored cells within the information area and a second part of a plurality of colored cells without biological indicator within the information area remains the same during reaction of the biological indicator, wherein the biological indicator is a microbial indicator that changes color in response to the amount of microbe.

2. A wound determination system, comprising:
a processing center;
a reader, being in communication connection with the processing center; and
the dressing of claim 1;
wherein the readable pattern layer is readable by the reader, and the reader transmits an image of the readable pattern layer into the processing center for determination.

3. The wound determination system according to claim 2, wherein the plurality of colored cells change color thereof according to a status of the wound, the processing center determines a result according to a color change degree or a color change area of the plurality of colored cells of the readable pattern layer, and the processing center generates a reminder signal according to the result.

4. The wound determination system according to claim 3, wherein the processing center has an area information of each of the plurality of positioning marks, and the processing center calculates a color change area information of the plurality of colored cells according to the area information.

5. The wound determination system according to claim 4, wherein the processing center calculates a proportion of an infected area of the wound according to the color change area information.

6. The wound determination system according to claim 3, wherein the result comprises a remaining effective time of the dressing, an infection degree of the wound, a healing degree of the wound, or a remaining recovery time of the wound.

7. The dressing according to claim 1, wherein the plurality of positioning marks and all of the plurality of colored cells form a machine readable pattern.

8. The dressing according to claim 7, wherein all of the plurality of colored cells comprise the biological indicator.

9. The dressing according to claim 7, wherein part of the plurality of colored cells comprises paint.

10. The dressing according to claim 1, wherein the plurality of colored cells are divided into a first group and a second group, the first group comprises the biological indicator, the second group and the plurality of positioning marks comprise paint, and the second group and the plurality of positioning marks form a machine readable pattern.

11. The dressing according to claim 1, wherein the plurality of colored cells are divided into a first group and a second group, the first group comprises a first biological indicator, the second group comprises a second biological indicator, and the first biological indicator and the second biological indicator react according to different conditions.

12. The dressing according to claim 1, wherein the biological indicator is made of a material used in an acid-base indicator, a chemical indicator, a bacterial indicator, an endospore indicator, a protein indicator, a peptide indicator, a DNA indicator, or an enzyme indicator.

* * * * *